United States Patent [19]

Sears et al.

[11] Patent Number: 4,476,140

[45] Date of Patent: Oct. 9, 1984

[54] COMPOSITION AND METHOD FOR TREATMENT OF GLAUCOMA

[75] Inventors: Marvin Sears, Branford; Joseph Caprioli, Hamden, both of Conn.

[73] Assignee: Yale University, New Haven, Conn.

[21] Appl. No.: 494,652

[22] Filed: May 16, 1983

[51] Int. Cl.$^3$ .............................................. A61K 31/35
[52] U.S. Cl. .................................................... 424/283
[58] Field of Search ........................................ 424/283

[56] References Cited

U.S. PATENT DOCUMENTS 3,631,039 12/1971 Andrews et al. ................... 544/149
4,118,508 10/1978 Bhat et al. ............................ 424/283
4,134,986 1/1979 Bajwa et al. ......................... 424/283

Primary Examiner—Douglas W. Robinson
Attorney, Agent, or Firm—Walter J. McMurray

[57] ABSTRACT

Topical administration of one of the polyoxygenated Labdanes of which forskolin is an example to the eyes produces lower intraocular pressure. The topical application to the eye produces no significant changes in blood pressure or pulse rate. The polyoxygenated Labdanes are effective agents for the treatment of glaucoma.

1 Claim, No Drawings

COMPOSITION AND METHOD FOR TREATMENT OF GLAUCOMA

FIELD OF THE INVENTION

The invention described herein relates to the use of polyoxygenated Labdanes, which the diterpene forskolin is an example, in a composition and in a method for the treatment of the eye disease glaucoma.

BACKGROUND OF THE INVENTION

Glaucoma is a disease of the eye often marked by increased intraocular pressure, resulting in atrophy of the ganglion cell layer of the retina and cupping of the disk which may result in blindness. At the present time, the only medical way to treat glaucoma is to lower the intraocular pressure of the eye with systemic anhydrase inhibitors, topical cholinomimetics or adrenergic agonists or antagonists. Polyoxygenated Labdanes, of which forskolin is an example, when applied topically to the eye are unique antiglaucoma agents with some superior properties over these presently employed antiglaucoma agents.

The object of the invention was to discover an antiglaucoma agent which minimized the side effects observed with the catecholamine agonist class of antiglaucoma agents. With prolonged use, this class of agents irritates the surface of the eye and decreases responsiveness and in some instances causes retinal edema. The carbonic anhydrase class of antiglaucoma agents must be given orally and exhibits significant systemic side effects. Timolol is a effective topical antiglaucoma agent but is contraindicated in patients with cardiac and pulmonary diseases and may at times exhibit tolerance.

In the therapy of glaucoma the aim is to reduce, reverse, prevent or arrest functional damage to the visual field. In practice, for the most part, the ophthalmologist measures intraocular pressure, makes certain assumptions about the connection between the intraocular pressure level and the risk for visual field damage, then proceeds to treat the pressure level in a way that may suit the eye, the individual, and his environment. There is the important consensus that intraocular pressure must usually be reduced from the level at which it is first confronted in the patient. That is the level at which damage has either occurred or the level thought to be too high for a particular eye to bear without the risk of functional loss. This pressure guide is the major therapeutic handle on the disease. Therefore, it is largely agreed that the more effective is the pressure reduced the better is the action of any particular drug.

The diterpene forskolin is isolated from Coleus forskohlii (syn. C. barbatus). Its chemical composition and its molecular structure are known (Bhat, Bajwa, Dornauer, de Souza, Fehlhaber, Tetrahedron Lett., 19,1669 (1977)). The compound forskolin in a purified and isolated form is disclosed in U.S. Pat. No. 4,088,659. The compound is characterized by a very good blood pressure lowering effect. It has peripheral vasodilation and mild central nervous system depressant activity. Due to its blood pressure lowering action the compound is suitable for the treatment of cardiac and circulatory diseases, for example, essential and malignant hypertonia, cardiac insufficiency, angina pectoris and disturbances of the peripheral circulation. The compound may be administered perorally or intraveneously.

The structural formula for forskolin is:

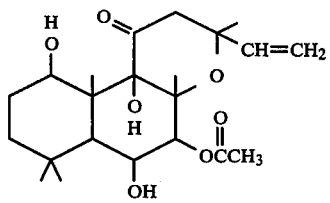

Another polyoxygenated Labdane named coleforsin has been isolated from plants belonging to the Labiatae family. That substance in purified and isolated form together with its use in a pharmaceutical preparation in and method for the treatment of cardiac or cardiovascular diseases is disclosed in U.S. Pat. No. 4,118,508. This substance has the structural formula:

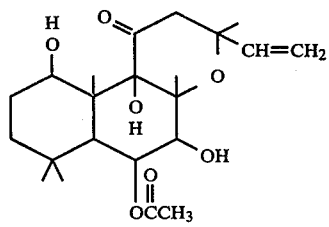

A series of synthetic derivatives related to forskolin and coleforsin named polyoxygenated Labdane derivatives are disclosed in U.S. Pat. No. 4,134,986. A pharmaceutical composition of these polyoxygenated Labdane compounds in the treatment of heart and circulatory disease and the method of treating these diseases with these substances is also claimed.

Research has shown (see e.g., Seamon, Padgett, Daly, Proc. Natl. Acad. Sci. U.S.A. 78(6), 3363 (1981)) that forskolin activates adenylate cyclase in membranes from brain and the tissues from rats to produce elevated levels of cyclic adenosine monophosphate (CAMP). Forskolin is unique in that its activation in intact cells is reversible whereas other activators of CAMP in intact cells such as cholera toxin produce only irreversible activation. Forskolin has been reported to activate adenylate cylase in cardiac tissue from guinea pigs (Metzger and Lindner, Arzneimittelforsch 31(8), 1248 (1981)) brain tissue from rats (Seamon, Padgett, Daly, supra), blowfly salivary glands (Letosch, Saito, Fain, Biochem. J. 204(1), 147 (1982)), adrenal glands of rats (Moriwaki, Itoh, Iida, Ichihara, Life-Sci. 30(25), 2235 (1982)), guinea pig thyroids, (Fradkin, Cook, Kilhoffer, Wolff, Endocrinology 111(3), 849 (1982)), epithelial preparations of amphibian skin and rat colon (Cuthbert, Spayne, B. J. Pharmacol, 76(1), 33(1982)), and human plalelets (Siesl, Daly, Smith, Mol Pharmacol. 21(3), 680 (1982)).

There are two approaches to reducing the intraocular pressure. One is the use a drug which is a secretory suppressant; that is, a drug that has an action to reduce intraocular pressure by reducing the rate of aqueous humor formation. Aqueous humor is the fluid which fills the anterior chamber of the eye and the posterior chamber in front of the lens. The second approach is to use a drug which decreases the resistance to outflow of the aqueous humor. These drugs are largely aimed at making the ciliary muscles work harder. Pilocarpine and related drugs are examples of these later agents. The intimate mechanisms of action of any of the new or old drugs used in the treatment of glaucoma is unknown. Until more is know about the metabolism of the normal and abnormal meshwork, a selection between the two approaches to therapy cannot be made. The therapy which is the subject of this invention reduces the intraocular pressure by reducing the net formation of aqueous humor.

The general mechanisms by which some of the early therapies lowered intraocular pressure can be understood in the light of the knowledge that beta adrenergic blockers lower intraocular pressure by reducing aqueous humor formation. Adrenergic receptors are molecules with which specific drugs, namely sympathomimetic drugs, interact in order to produce an effect. Adrenergic receptors are classified as alpha or beta, the latter of two types: $beta_1$ and $beta_2$. An agonist is a drug which interacts with receptors and elicits a response. An antagonist is substance which interacts with receptors but produces no response. In reviewing prior glaucoma therapies, the agonists will be discussed first.

Adrenalin or epinephrine was first tried by Darier in 1894 by subconjunctival injection, and then more consistently since the 1920's when Hamburger applied the drug topically. Efforts to develop a less irritating drug for topical use have included producing bitartrate, then borate, and then hydrochloride salts of the drug in various vehicles. Additional recent efforts have been to increase the penetration of the drug and reduce its irritation by utilizing the principle of a pro drug. The compound dipuvalyl epinephrine was produced (Chem. and Eng. News 52:26 (1974). This drug is lipid soluble, penetrates the corneal epithelium and is hydrolyzed in the cornea to active epinephrine (Anderson, et al, Invest. Ophthalmol. Vis. Sci. 19:817 (1970)). A study of adult response curves with this drug indicated that the curve was shifted to the left about tenfold. In other words, one tenth of the amount of base, epinephrine, is required to exert the same effort. A pro drug of norepinephrine has also been found to be effective (Stewart, et al, Ann. Ophthalmol 13,1279 (1981)). After about 4 or 5 years of therapy with topical epinephrine about 80% of the patients exhibit an external ocular reaction that very often requires cessation of therapy. The pro drugs have not been used for as long as 5 years, but at the moment current data indicates that a significant incidence of external reaction occurs but that it may be somewhat reduced (Wandel and Spinak, Ophthalmology (Rochester) 88,259 (1981)). Epinephrine probably has both alpha and beta effects and acts both to reduce inflow as well as to increase true outflow.

Marijuana and related compounds have been mentioned as agents for the treatment of glaucoma. Smoking marijuana causes intraocular pressure to fall in normal volunteers or glaucoma patients. The primary active ingredient in marijuana, delta 9-tetrahydrocannabinol (delta 9-THC) causes small reductions in intraocular pressure after oral or intravenous administration. Topical application of delta 9-THC in a single dose did not cause any significant fall in intraocular pressure (Green, et al, Arch. Ophthalmol 100,625 (1982)). Nabilone is a synthetic, crystalline benzopyran that resembles the cannabinol. Oral administration of 0.5 to 2 mgs of Nabilone to patients with open angle glaucoma reduced the intraocular pressure an average of 28%. Nabilone administered topically in a 0.1 mg dose to both eyes of albino rabbits, lowered the intraocular pressure an average of 25% with a peak reaction after one hour. Tolerance, however, developed after one week of topical applications (Newell, et al, Trans. Am. Acad. Ophthal. Otol. 86,156 (1979)).

Isoproterenol, a beta adrenergic agonist, when administered topically, reduces eye pressure in humans by reducing aqueous humor formation. D-isoproterenol lowers eye pressure in rabbits (Seidehamel, Am. J. Opthalmol. Vis. Sci., 15:113 (1976)). Several beta agonist especially $beta_2$ agonists have been shown to lower intraocular pressure in animals (see for example Colasanti and Trotter, Invest. Ophthalmol. Vis. Sci., 20,69 (1981)). Ross and Drance (Arch. Ophthalmol. 83,39 (1970)) pointed out the lack of effect of isoproterenol with chronic administration. Both tachyphylaxis (acute tolerance within minutes wherein repeated doses in a short period of time elicit sequentially smaller and smaller responses) and tolerance (decreased responsiveness to the pharmacologic effect of a drug from previous exposure to it or a related one) occur. Other toxic effects include local ocular hyperemea and systemic side effects including a brisk tachycardia.

Turning to beta antagonists, dichloroproterenol, an analog is isoproterenol, lowered eye pressure in rabbits and humans but only slightly, similar to the mild effect of beta blockers of later development. Patients who were afflicted with glaucoma when treated for systemic hypertension with beta adrenergic blocking drugs were observed to experience reduced intraocular pressure to a slight to moderate degree. Topical applications of propranolol, a beta blocker, produced slight reductions in eye pressure but its local anesthetic properties made the drug unsuitable for topical treatment of glaucoma. Timolol was the first beta blocker to produce dramatic reductions in intraocular pressure.

Timolol, a nonselective beta blocker, reduces eye pressure by reducing net aqueous inflow (Yablonski, et al, Exp. Eye Res. 27, 135 (1978)), Coakes, et al. Arch. Ophthalmol. 96,2045 (1978)). The advantage of Timolol is its efficacy. Its disadvantage is that it can antagonize both $beta_1$ and $beta_2$ receptor in cardiac and pulmonary tissue. It is, therefore, contraindicated in patients with bronchospastic disease, with congestive heart failure, and, probably also, contraindicated in patients who have certain cardiac arrhythmias or heart block.

It is not known how the topical application of both beta agonists and beta antagonist lower intraocular pressure. On the molecular level stimulation of the beta adrenergic receptor leads to activation of membrane bound adenyl cyclase and to an accelerated rate of production of intracellular cyclic adenosine monophosphate (CAMP). Other agents, although not clinically acceptable such as organic fluorides, cholera toxin, and the preparations of the glycoprotein hormones which activate adenyl cyclase lower intraocular pressure by reducing net aqueous humor flow (see for example Sears, Int. Ophthalmol., 6, 181 (1983)). Therefore, it seems likely that activation of the beta receptors and not its blockade is related to a reduction in net aqueous humor flow. It seems likely that beta blockers reduce aqueous humor formation by mechanisms in addition to their beta blocking action. Understanding the basic mechanism of action of a drug does not mean that it is understood how the drug works in the context of clinical therapy.

Another clinically effective method to treat glaucoma is with a class of agents which act as carbonic anhydrase inhibitors. These agents such as acetazolamide, ethoxzolamide, methazolamide and dichlorophenamide are administered orally or intravenously (acetazolamide). These agents can produce mild systemic acidosis and urinary calculi and annoying side effects such as gastrointestinal discomfort and paresthesias. These agents are ineffective when administered topically due to poor penetration of the cornea. For effective penetration into the eye, the agent must have both hydrophilic and lipophilic characteristics. The use of pro drug or liposomes, vesicles of phospholipids, as carrier vehicles to cause more effective penetration of drugs into cells may be applied to the eye (Schaeffer and Krohn, Invest. Ophthalmol. Vis. Sci., 22,220 (1982)).

To summarize, many types of agents are used in the treatment of glaucoma. Some are applied topically, some orally and some intravenously. Some of the agents produce tolerance on extended usage, produce annoying side effects or are contraindicated for patients suffering cardiac and/or pulmonary diseases.

SUMMARY OF THE INVENTION

This invention provides a new and improved method of reducing intraoccular pressure. One object of the invention is that the method be easily performed by human patients or on human patients experiencing elevated intraoccular pressure. A second object of the invention is that the method be effective in reducing intraoccular pressure. A third object of the invention is that the method be effective in reducing intraoccular pressure after prolonged application of the method. A fourth objective of the invention is that the method not sensitize the tissue of the eye. The final objective of the invention is that utilization of the method not produce annoying or adverse physiological effects on the patient.

Forskolin represents a new class of antiglaucoma agents which when applied topically to the eye produces a rapid reduction in intraocular pressure while at the same time producing no observable change in the patient's blood pressure or pulse. Repeated topical applications of forskolin does not appear to result in tolerance. The efficacy of forskolin is comparable to Timolol. The collective properties of forskolin make it an effective agent for the treatment of glaucoma when applied in accordance with the invention.

DETAILED DESCRIPTION OF THE INVENTION

In the treatment of glaucoma, a polyoxygenated Labdane compound of which forskolin is an example is administered topically to the eye. For topical application to the eye the polyoxygenated Labdane compound is used in combination with a pharmaceutically acceptable carrier such as aqueous methylcellulose. The combination may be in the form of a suspension, solution, ointment, emulsion or an ocusert. The more favored combination is that which promotes prolonged contact of the polyoxygenated Labdane compound with the eye. The most favored combination is that which promotes the penetration into the eye of the polyoxygenated Labdane compound. This most favored combination is produced by the use in the combination of a drug such as benzalkonium chloride which facilitates the penetration of the eye by other drugs or by converting a polyoxygeneted Labdane compound into a pro drug such as the dipivalyl derivative. Any derivative of a polyoxygenated Labdane compound which makes the drug more lyophilic but which is hydrolyzed in the cornea would be suitable.

A physiologically effective amount of a pharmacologically acceptable combination is applied to the eye as often as required. A concentration of a polyoxygenated Labdane compound in the range of 0.1% to 4% has been physiologically effective when administered as a topical suspension to the eye. The most preferred range of concentration of the polyoxygenated Labdane compound is 1% to 4%. The number of administrations per day is dependent on the concentration of the polyoxygenated Labdane compound administered. A 1% suspension of a polyoxygenated Labdane compound administered to human volunteers was effective in reducing intraocular pressure on the average of six hours. Therefore, for effective control of intraocular pressure three to four topical administrations per day are needed.

A polyoxygenated Labdane may be administered to patients in combination with other antiglaucoma agents in the treatment of glaucoma.

The following examples illustrate the invention:

EXAMPLE 1

A 1% suspension of forskolin in aqueous methylcellulose when administered topically as drops in a volume of 50 microliters (ul.) to the eye of a rabbit produced an observable reduction in intraocular pressure within one hour which maximized between three and four hours. The effect persisted with diminishing effectiveness for eight to ten hours. Every six hours administration of 1% forskolin suspension for fifteen days did not result in diminished effectiveness i.e., tolerance for the drug was not observed.

EXAMPLE 2

An administration of a drop (50 ul.) of 1% suspension of forskolin in aqueous methylcellulose to the eyes of ten monkeys reduced intraocular pressure significantly after one hour with maximum effect after two to three hours. The effect persisted with diminishing effectiveness for at least seven hours.

EXAMPLE 3

A topical administration of 50 ul. of a 1% suspension of forskolin in methylcellulose to the eyes of 10 humans, ranging in age from 26 to 58 (mean age of 42), produced dramatic and significant lower intraocular pressures in 6 eyes, slightly in 2 eyes and not at all in 2 eyes, one of which had very low intraocular pressure to start. The reduced intraocular pressure lasted for at least 4 hours. Neither the blood pressure nor the pulse rate of each of the individuals was significantly affected during the period of observation.

Having described the invention we claim:

1. A method for treating elevated intraocular pressure or glaucoma which comprises topically administering to a patient suffering therefrom a therapeutically effective amount of a material selected from the group consisting of forskolin, coleforsin and polyoxygenated Labdane derivatives.

* * * * *